United States Patent
Shimoda et al.

(10) Patent No.: US 9,687,537 B2
(45) Date of Patent: Jun. 27, 2017

(54) DENDRITIC CELL VACCINES FOR ASPARAGINYL-β-HYDROXYLASE EXPRESSING TUMORS

(75) Inventors: Masafumi Shimoda, Providence, RI (US); Jack R. Wands, East Greenwich, RI (US)

(73) Assignee: Rhode Island Hospital, Providence, RI (US)

( * ) Notice: Subject to any disclaimer, the term of this patent is extended or adjusted under 35 U.S.C. 154(b) by 13 days.

(21) Appl. No.: 12/842,494

(22) Filed: Jul. 23, 2010

(65) Prior Publication Data

US 2011/0076290 A1  Mar. 31, 2011

Related U.S. Application Data

(60) Provisional application No. 61/228,429, filed on Jul. 24, 2009, provisional application No. 61/231,127, filed on Aug. 4, 2009, provisional application No. 61/239,288, filed on Sep. 2, 2009, provisional application No. 61/240,745, filed on Sep. 9, 2009.

(51) Int. Cl.

| | |
|---|---|
| A61K 39/00 | (2006.01) |
| A61K 35/00 | (2006.01) |
| C12N 5/0784 | (2010.01) |
| C12N 9/02 | (2006.01) |

(52) U.S. Cl.
CPC ........ *A61K 39/0011* (2013.01); *C12N 5/0639* (2013.01); *C12N 9/0071* (2013.01); *A61K 2039/5154* (2013.01); *A61K 2039/5158* (2013.01); *A61K 2039/545* (2013.01); *C12N 2500/90* (2013.01); *C12N 2501/22* (2013.01); *C12N 2501/23* (2013.01); *C12N 2501/24* (2013.01); *C12N 2501/52* (2013.01)

(58) Field of Classification Search
None
See application file for complete search history.

(56) References Cited

U.S. PATENT DOCUMENTS

| | | | |
|---|---|---|---|
| 6,372,262 B1* | 4/2002 | Peled et al. | 424/531 |
| 6,753,328 B2 | 6/2004 | Wands et al. | |
| 6,783,758 B2 | 8/2004 | Wands et al. | |
| 6,797,696 B2 | 9/2004 | Wands et al. | |
| 6,812,206 B2 | 11/2004 | Wands et al. | |
| 6,815,415 B2 | 11/2004 | Wands et al. | |
| 6,835,370 B2 | 12/2004 | Wands et al. | |
| 7,122,541 B2 | 10/2006 | Wands et al. | |
| 7,413,737 B2 | 8/2008 | Wittrup et al. | |
| 2002/0110559 A1* | 8/2002 | Wands et al. | 424/146.1 |
| 2004/0203143 A1* | 10/2004 | Tjoa et al. | 435/372 |
| 2005/0020520 A1* | 1/2005 | Lai et al. | 514/44 |
| 2005/0113329 A1 | 5/2005 | Wands et al. | |
| 2005/0123545 A1* | 6/2005 | Wands et al. | 424/146.1 |
| 2006/0057129 A1 | 3/2006 | Lebkowski et al. | |
| 2011/0076290 A1 | 3/2011 | Shimoda et al. | |

FOREIGN PATENT DOCUMENTS

| | | |
|---|---|---|
| WO | WO-0135102 A2 | 5/2001 |
| WO | WO-2006022407 A1 | 3/2006 |
| WO | WO-2006126008 A2 | 11/2006 |
| WO | WO2007/067782 * | 6/2007 |

OTHER PUBLICATIONS

Dauer et al (Journal of Immunology, 2003, vol. 170, pp. 4069-4076).*
Gehring et al (Journal of Immunological Methods, Jan. 2008, vol. 332, pp. 18-30).*
Gamvrellis et al, Immunology and Cell Biology, 2004, vol. 82, pp. 506-516.*
Scheicher et al ('The Th1 Lymphokine Interferon-γ is a Potent Upregulator of Dendritic Cells with Phagocytic Capacity in GM-CSF Supplemented Bone Marrow Cultures', In Dendritic Cells in Fundamental and Clinical Immunology, Ricciardi-Castagnoli, Ed., New York, 1997, pp. 221-225).*
The abstract of Jie et al (Zhonghua yi xue za zhi, 2004, vol. 84, pp. 932-936).*
Bai et al (International Journal of Oncology, 2002, vol. 20, pp. 247-253).*
Audran et al (Vaccine, 2003, vol. 21, pp. 1250-1255).*
Holtl et al, Journal of Urology, 1999, vol. 161, pp. 777-782.*
ClinicalTrials.gov, downloaded from the Web on Jul. 14, 2016.*
Calderhead et al., "Cytokine Maturation Followed by CD40L mRNA Electroporation Results in a Clinically Relevant Dendritic Cell Product Capable of Inducing a Potent Proinflammatory CTL Response", *J. Immunother.*, 31(8):731-741 (2008).
Hoffmann et al., "Proinflammatory Cytokines and CD40 Ligand Enhance Cross-Presentation and Cross-Priming Capability of Human Dendritic Cells Internalizing Apoptotic Cancer Cells", *J. Immunother.*, 24(2):162-171 (2001).
Ince et al., "Overexpression of Human Aspartyl (Asparaginyl) β-Hydroxylase Is Associated with Malignant Transformation", *Cancer Res.*, 60(5):1261-1266 (2000).
Knippertz et al., "Generation of Human Dendritic Cells That Simultaneously Secrete IL-12 and Have Migratory Capacity by Adenoviral Gene Transfer of hCD40L in Combination With IFN-γ", *J. Immunother.*, 32(5):524-538 (2009).
Luu et al., "Prognostic value of aspartyl (asparaginyl)-β-hydroxylase/humbug expression in non-small cell lung carcinoma", *Human Pathology*, 40(5):639-644 (2009).
Shimoda et al., "Induction of Antigen Specific Immunity Against HCC With Aspartate-β-Hydroxylase and Dendritic Cell Vaccine", *Hepatol.*, 50(4):1094A (2009) (Abstract Only).
Xu et al., "High-avidity antitumor T-cell generation by toll receptor 8-primed, myeloid-derived dendritic cells is mediated by IL-12 production", *Surgery*, 140(2):170-178 2006).
Butterfield et al., "A phase I/II trial testing immunization of hepatocellular carcinoma patients with dendritic cells pulsed with four alpha-fetoprotein peptides." Clinical Cancer Research 12:2817-2825 (2006).

(Continued)

*Primary Examiner* — Karen Canella
(74) *Attorney, Agent, or Firm* — Mintz Levin Cohn Ferris Glovsky and Popeo, P.C.; Ingrid A. Beattie

(57) ABSTRACT

A vaccine containing AAH-loaded mature dendritic cells for treatment of AAH-expressing tumors in mammalian subjects. A method of producing primed dendritic cells is carried out by contacting isolated dendritic cells with an antigen such as AAH. Following the antigen-contacting step, the dendritic cells are contacted with a combination of cytokines such as GM-CSF and IFN-γ.

22 Claims, 9 Drawing Sheets

(56) References Cited

OTHER PUBLICATIONS

Butterfield et al., "T-cell responses to HLA-A*0201 immunodominant peptides derived from alpha-fetoprotein in patients with hepatocellular cancer." Clin. Cancer Res., 1(9):5902-5908 (2003).

"Cancer Treatment by Dendritic Cells" Inflammation and Immunity, 9(4):448-454 (2001).

Dauer et al., "Mature dendritic cells derived from human monocytes within 48 hours: a novel strategy for dendritic cell differentiation from blood precursors." J. Imm. vol. 170: 4069-46 (2003).

Celluzzi et al., "Peptide-pulsed dendritic cells induce antigen-specific CTL-mediated protective tumor immunity." J Exp Med. 183:283-287 (1996).

Song et al., "The distribution and expression pro-files of Aspartyl/Asparaginyl beta-hydroxylase (ASPH) in some tumorous cell lines and tissues." Chin J Cell Mol Immunol. 26(2):141-144 (2010).

Tsukada et al., "Therapeutic effect of treatment with polyclonal or monoclonal antibodies to alpha-fetoprotein that have been conjugated to daunomycin via a dextran bridge: studies with an alpha-fetoprotein-producing rat hepatoma tumor model." Cancer Res. 47:4293-4295 (1987).

Wang et al., "Overexpression of aspartyl-(asparaginyl)-beta-hydroxylase in hepatocellular carcinoma is associated with worse surgical outcome." Hepatology, 52:164-173 (2010).

* cited by examiner

DENDRITIC CELL VACCINES FOR ASPARAGINYL-β-HYDROXYLASE EXPRESSING TUMORS

RELATED APPLICATIONS

This application claims priority to U.S. provisional patent application 61/228,429, filed Jul. 24, 2009, U.S. provisional patent application 61/231,127, filed Aug. 4, 2009, U.S. provisional application 61/239,288, filed Sep. 2, 2009 and U.S. provisional application 61/240,745, filed Sep. 9, 2009, the entire contents of which are hereby incorporated by reference.

REFERENCE TO A "SEQUENCE LISTING"

The sequence listing material in the text file entitled "21486_593001US_Sequence_Listing_ST25.txt" (10,093 bytes), which was created on Nov. 18, 2010, is herein incorporated by reference in its entirety.

BACKGROUND OF THE INVENTION

Liver cancer including hepatocellular and cholangiocellular carcinoma is one of the most common cancers in the world. In the United States, liver cancer is the fifth common cause of cancer death in men and the ninth in women. In spite of the dramatic progress in diagnosis and local control of liver cancer, the mortality rate in the United States has been increasing constantly. One of the reasons for the increasing mortality might be that, unlike other cancers including breast and colorectal cancers, liver cancer is resistant to systemic treatment such as chemotherapy. Therefore, there is no effective treatment of liver cancer once it becomes a systemic disease.

SUMMARY OF THE INVENTION

The invention provides a solution to the longstanding problem of an alternative to chemotherapy for treatment of patients diagnosed with cancer. A method of reducing growth of an aspartyl (asparaginyl)-β-hydroxylase (AAH or ASPH)-expressing tumor in a subject involves administering to the subject an isolated mature AAH-loaded dendritic cell or population of cells. Growth of an AAH-expressing tumor is reduced after administration of such a dendritic cell vaccine. For example, tumor growth and tumor burden is reduced by 10%, 20%, 50%, 75%, 2-fold, 5-fold, 10-fold, or more. The methods are used to reduce and eliminate AAH-expressing tumors from mammalian subjects, such as human patients. The compositions and methods are also suitable for use in companion animals and livestock, e.g., human, canine, feline, equine, bovine, or porcine subjects.

AAH-expressing tumors include most tumor types such as tumors of gastrointestinal tissues (e.g., esophagus, stomach, colon), pancreas, liver (e.g., cholangiocellular carcinoma, hepatocellular carcinoma), breast, prostate, cervix, ovary, fallopian tube, larynx, lung, thyroid, gall bladder, kidney, bladder, and brain (e.g., glioblastoma) as well as numerous others described below. AAH-expressing tumors include primary tumors that express and increased level of AAH compared to normal tissue as well as tumors that arise by metastasis from such AAH-overexpressing primary tumors.

The dendritic cells used in the vaccination method are preferably activated ex vivo with a combination of cytokines comprising GM-CSF and IFN-γ prior administering them to the subject. The latter step yields a population of dendritic cells with improved anti-tumor activity. An improved method of producing primed dendritic cells is carried out by contacting isolated dendritic cells with an antigen such as AAH or a combination of tumor antigens such as AAH and α-fetoprotein (AFP) and treating the cells to yield a population of matured and activated antigen-presenting cells. Following the antigen-contacting step, the dendritic cells are contacted with the combination of cytokines. For example, the combination comprises GM-CSF and IFN-γ. In other examples, the combination further comprises IL-4. Optionally, the combination comprises CD40L. The dendritic cells are contacted with the combination of cytokines for at least 10 hours (e.g., 12, 24, 36, 40, 48 hours or more). The antigen is in a soluble form or bound to a solid support. For example, the solid support comprises a polystyrene bead such as a biodegradable bead or particle. Dendritic cells are obtained from a subject by known methods such as leukapheresis or cytopheresis.

The subject from which the cells are obtained is suffering from or at risk of developing cancer. For example, the patient has been diagnosed with a tumor such as an AAH-expressing tumor. Patients who are at risk of developing cancer such as AAH-bearing tumors include those with a family history of individuals who have been identified with such a cancer.

Also within the invention is a vaccine composition comprising primed dendritic cells produced as described above. The vaccine is useful to inhibit tumor growth, prevent tumor growth, and inhibit or reduce metastasis. A method of inhibiting tumor growth in a mammal is carried out by identifying a subject suffering from an AAH-bearing tumor, and administering to the subject autologous dendritic cells, which have been primed according to the method described above. A method of preventing development of a tumor in a mammal, comprises the step of identifying a subject at risk of developing an AAH-bearing tumor (such as one with a family history of cancer), and administering to the subject the antigen-primed and activated autologous dendritic cells. A method of preventing metastasis of an AAH-bearing tumor is carried out by identifying a subject suffering from an AAH-bearing tumor, and administering to the subject autologous dendritic cells, as described above.

The polypeptides and other compositions of the invention are purified. For example, a substantially pure AAH polypeptide variant thereof is preferably obtained by expression of a recombinant nucleic acid encoding the polypeptide or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, AAH. Purity is measured by any appropriate method, e.g., column chromatography, polyacrylamide gel electrophoresis, or HPLC analysis. Accordingly, substantially pure polypeptides include recombinant polypeptides derived from a eucaryote but produced in *E. coli* or another procaryote, or in a eucaryote other than that from which the polypeptide was originally derived.

Dendritic cells or other cells, e.g., immune cells such as macrophages, B cells, T cells, used in the methods are purified or isolated. With regard to cells, the term "isolated" means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

The methods of generated antigen-primed DCs has several advantages over earlier methods. The cells are not only antigen-loaded but the subsequent cytokine incubation yield superior activated antigen-primed antigen presenting cells with improved anti-tumor and anti-metastatic activity.

These and other capabilities of the invention, along with the invention itself, will be more fully understood after a review of the following figures, detailed description, and claims. All references cited herein are hereby incorporated by reference.

DETAILED DESCRIPTION

Figure 1:
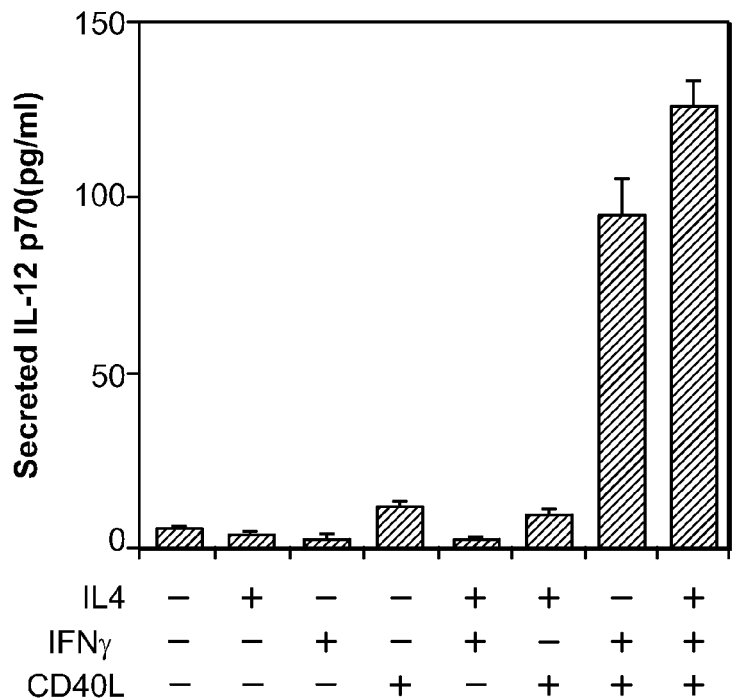
FIG. 1 is a bar graph showing IL-12 production by isolated DCs.

AAH is a protein, the expression of which is associated with a number of cancer types (see, e.g., U.S. Pat. No. 6,815,415; U.S. Pat. No. 6,812,206; U.S. Pat. No. 6,797,696; U.S. Pat. No. 6,783,758; U.S. Pat. No. 6,835,370; and U.S. Pat. No. 7,094,556). Over-expression of HAAH has been detected by immunohistochemical staining (IHC) in numerous cancers lung (e.g., adenocarcinoma, bronchioalveolar carcinoma, and other non-small cell lung cancers such as squamous cell carcinoma subtype (Luu et al., 2009, Hum. Pathol. 40:639-644), liver (e.g., hepatocellular carcinoma, cholangiocarcinoma, and cancer of biliary epithelial cells (Wang et al., 2010, Hepatology 52:164-173), gastrointestinal tissues (e.g., colon, stomach, esophagus), pancreas, prostate, ovary, bile duct, breast, kidney, bladder, and brain (e.g., glioblastoma and neuroblastoma. Another survey of tumor tissue samples and cell lines confirmed AAH expression in the following additional cancers (compared to non-cancer tissues): laryngeal carcinoma, cervical cancer, fallopian tube cancer, liver cancer (e.g., cholangiocarcinoma), kidney cancer, breast cancer, cervical cancer, ovarian cancer, Fallopian tube carcinoma, laryngeal cancer, lung cancer, thyroid cancer, pancreatic cancer, thymic carcinoma, prostate cancer, bladder cancer, esophageal cancer, gastric cancer, gallbladder cancer, colon cancer, and rectal cancer (Song et al., 2010, Chinese J. of Cell. and Mol. Immunol. 26: 141-144). HAAH is highly specific for cancer; it has been detected by immunohistochemistry in >99% of tumor specimens tested (n>1000) and is not present in adjacent non-affected tissue, or in tissue samples from normal individuals.

Immunotherapy using AAH-primed cells is administered to patients with tumors that express AAH on their cell surface. Such tumors include liver cancers such as hepatocellular carcinoma and cholangiocarcinoma, as well as adenocarcinomas of the breast and colon. Such a therapeutic strategy is useful for not only treatment but prevention of cancers.

Prior to the invention, there has been no effective systemic treatment of liver cancer, in spite of the advances in diagnosis and local control of the disease. Immunotherapy is used to treat systemic and localized liver cancer, because of its specificity.

Dendritic cell vaccines using AAH were found to cure established hepatocellular carcinoma in immunocompetent mice. AAH dendritic cell vaccines reduce growth of AAH-expressing tumors to decrease tumor burden and eradicate tumors in humans as well.

Immunotherapy

Immunotherapy of malignant tumors is attractive in terms of the specific response to tumor cells. A rationale for immunotherapy is that cancer cells are replete with potential antigens, which become immunogenic when presented by antigen-presenting cells to helper and cytotoxic T cells. Immunotherapy for liver cancer, whether systemic or not, is a viable clinical approach, because liver cancer cells express several tumor-associated proteins, which are not or only slightly expressed in normal tissues. For example, AFP, which is not expressed in adult tissues, is extensively expressed in hepatocellular carcinoma (HCC). Several studies have shown that AFP-specific immune reaction can be induced not only in mice but also in humans. However, a clinical trial of HCC immunotherapy that targets AFP did not show even partial tumor responses. Some possible reasons are: because AFP is not involved in cancer progression, cancer cells that do not express AFP dominated during APP-targeting immunotherapy. In order for HCC cells to be recognized by AFP-responsive T cells, AFP should be presented on the cell surface with major histocompatibility complex (MHC) class I molecule, because AFP is not distributed on the cell surface. However, as MHC class I molecules are often down-regulated in many cancer cells, AFP may not be appropriately recognized by the T cells. To overcome the problems of liver cancer immunotherapy, studies were undertaken to identify another antigen that is associated with liver cancer to be used to primed cells for cell-based therapy. Given the results using AFP as an antigen, the anti-tumor results with AAH were surprising.

AAH, also known as ASPH, is strongly expressed in hepatocellular and cholangiocellular carcinoma, but is not expressed in normal cell counterparts of those tissue types. AAH is therefore a tumor-associated protein. AAH is useful for immunotherapy of liver cancer, because of its unique nature. First, AAH confers cancer cells on motility, which is associated with cancer metastasis; thus, therapy targeting AAH-expressing cells is effective to suppress metastatic lesions as well as the primary tumor. Second, because AAH is membrane protein, most part of which is exposed to extracellular space, it is easier for immune cells to access to the protein even when class I molecules are down-regulated. Third, other than AAH, no antigenic protein specific to cholangiocellular carcinoma is known. Thus, AAH is uniquely qualified as a target molecule of immunotherapy against liver cancer.

An immunotherapy approach involves injection of dendritic cells (DCs) loaded with the protein of interest. DCs are specialized cells that capture, process, and present antigens to T cells to induce and control T cell-mediated immunity. DCs are widely used to immunize not only laboratory animals but also tumor-bearing patients. The methods described herein include a DC-based immunization for induction of immunity against AAH. The present methods improve upon a previously described method for generating immunogenic mouse DCs loaded with protein of interest (Gehring et al., 2008, J. Immunol. Meth. 332:18-30) in at least two ways. One is that to stimulate DCs, lipopolysaccharides (LPS) was previously used, a strong pyrogen that may be inappropriate for in vivo use. Second is that DC stimulation was relatively weak, judging by IL-12 secretion by DCs, and by the expression of various surface DC markers. Improvements were therefore made to the method for the generation of immunogenic DCs.

Dendritic Cell Vaccines

The most promising approach for HCC immunotherapy is the one using DCs, as they have a strong capacity of inducing T cell-mediated tumor immunity. DCs are derived from hematopoietic cells, and are specialized to capture and process antigens, converting proteins to peptides that are presented on MHC molecules and recognized by T cells. DCs strongly induce and control T-cell mediated immunity.

DC-based immunotherapy is based on the fact that tumors are replete with potential antigens, and these become immunogenic when presented by DCs. DCs are obtained from a subject, e.g. by cytopheresis. The cells, which are now ex vivo are loaded (i.e., contacted) with tumor antigens (e.g., tumor cell lysates; apoptotic or necrotic tumor cells; recombinant, synthetic, or purified tumor antigen peptide or protein; or nucleic acid such as RNA encoding tumor antigens), stimulated for maturation, and re-injected into patients to induce strong T-cell immunity.

AAH Tumor Antigen

AAH is type II membrane protein with a catalytic domain in a C-terminal region. Most parts of the protein are located at the outside of the cell membrane, allowing the access of immune cells to this protein. AAH protein is strongly expressed in HCCs, cholangiocarcinomas, and adenocarcinomas of breast or colon origin, and is barely detectable or completely undetectable in normal tissue counterparts. Thus, AAH is an ideal target molecule for DC-based immunotherapy of HCC and other AAH-bearing tumors.

Overexpressed AAH in tumor cells increases the cell motility, which confers malignant phenotype on tumor cells. A clinicopathological study on HCC revealed that AAH overexpression is associated with histological grade and intrahepatic metastasis. Therefore, targeting the AAH-expressing tumor cell population suppresses the development and progression of AAH-bearing tumors.

TABLE 1

Amino acid sequence of Human AAH

```
    MAQRKNAKSS GNSSSSGSGS GSTSAGSSSP GARRETKHGG HKNGRKGGLS GTSFFTWFMV
 61 IALLGVWTSV AVVWFDLVDY EEVLGKLGIY DADGDGDFDV DDAKVLLGLK ERSTSEPAVP
121 PEEAEPHTEP EEQVPVEAEP QNIEDEAKEQ IQSLLHEMVH AEHVEGEDLQ QEDGPTGEPQ
181 QEDDEFLMAT DVDDRFETLE PEVSHEETEH SYHVEETVSQ DCNQDMEEMM SEQENPDSSE
241 PVVEDERLHH DTDDVTYQVY EEQAVYEPLE NEGIEITEVT APPEDNPVED SQVIVEEVSI
301 FPVEEQQEVP PETNRKTDDP EQKAKVKKKK PKLLNKFDKT IKAELDAAEK LRKRGKIEEA
361 VNAFKELVRK YPQSPRARYG KAQCEDDLAE KRRSNEVLRG AIETYQEVAS LPDVPADLLK
421 LSLKRRSDRQ QFLGHMRGSL LTLQRLVQLF PNDTSLKNDL GVGYLLIGDN DNAKKVYEEV
481 LSVTPNDGFA KVHYGFILKA QNKIAESIPY LKEGIESGDP GTDDGRFYFH LGDAMQRVGN
541 KEAYKWYELG HKRGHFASVW QRSLYNVNGL KAQPWWTPKE TGYTELVKSL ERNWKLIRDE
601 GLAVMDKAKG LFLPEDENLR EKGDWSQFTL WQQGRRNENA CKGAPKTCTL LEKFPETTGC
661 RRGQIKYSIM HPGTHVWPHT GPTNCRLRMH LGLVIPKEGC KIRCANETRT WEEGKVLIFD
721 DSFEHEVWQD ASSFRLIFIV DVWHPELTPQ QRRSLPAI
```

(SEQ ID NO: 1; GENBANK Accession No. S83325; His motif is underlined; conserved sequences within the catalytic domain are designated by bold type; catalytic domain comprises residues 650-700 of SEQ ID NO: 1).

TABLE 2

Human AAH cDNA sequence

```
    cggaccgtgc aatggcccag cgtaagaatg ccaagagcag cggcaacagc agcagcagcg
 61 gctccggcag cggtagcacg agtgcgggca gcagcagccc cggggcccgg agagagacaa
121 agcatggagg acacaagaat gggaggaaag gcggactctc gggaacttca ttcttcacgt
181 ggtttatggt gattgcattg ctgggcgtct ggacatctgt agctgtcgtt tggtttgatc
```

TABLE 2-continued

Human AAH cDNA sequence

```
 241 ttgttgacta tgaggaagtt ctaggaaaac taggaatcta tgatgctgat ggtgatggag 301 attttgatgt ggatgatgcc aaagttttat taggacttaa agagagatct acttcagagc 361 cagcagtccc gccagaagag gctgagccac acactgagcc cgaggagcag gttcctgtgg 421 aggcagaacc ccagaatatc gaagatgaag caaaagaaca aattcagtcc cttctccatg 481 aaatggtaca cgcagaacat gttgagggag aagacttgca caagaagat ggacccacag 541 gagaaccaca acaagaggat gatgagtttc ttatggcgac tgatgtagat gatagatttg 601 agaccctgga acctgaagta tctcatgaag aaaccgagca tagttaccac gtggaagaga 661 cagtttcaca agactgtaat caggatatgg aagagatgat gtctgagcag gaaaatccag 721 attccagtga accagtagta gaagatgaaa gattgcacca tgatacagat gatgtaacat 781 accaagtcta tgaggaacaa gcagtatatg aacctctaga aaatgaaggg atagaaatca 841 cagaagtaac tgctccccct gaggataatc ctgtagaaga ttcacaggta attgtagaag 901 aagtaagcat ttttcctgtg gaagaacagc aggaagtacc accagaaaca aatagaaaaa 961 cagatgatcc agaacaaaaa gcaaaagtta agaaaaagaa gcctaaactt ttaaataaat 1021 ttgataagac tattaaagct gaacttgatg ctgcagaaaa actccgtaaa aggggaaaaa 1081 ttgaggaagc agtgaatgca tttaaagaac tagtacgcaa ataccctcag agtccacgag 1141 caagatatgg gaaggcgcag tgtgaggatg atttggctga agaggagga agtaatgagg 1201 tgctacgtgg agccatcgag acctaccaag aggtggccag cctacctgat gtccctgcag 1261 acctgctgaa gctgagtttg aagcgtcgct cagacaggca acaatttcta ggtcatatga 1321 gaggttccct gcttaccctg cagagattag ttcaactatt tcccaatgat acttccttaa 1381 aaaatgacct tggcgtggga tacctcttga taggagataa tgacaatgca aagaaagttt 1441 atgaagaggt gctgagtgtg acacctaatg atggctttgc taaagtccat tatggcttca 1501 tcctgaaggc acagaacaaa attgctgaga gcatcccata tttaaaggaa ggaatagaat 1561 ccggagatcc tggcactgat gatgggagat tttatttcca cctgggggat gccatgcaga 1621 gggttgggaa caaagaggca tataagtggt atgagcttgg gcacaagaga ggacactttg 1681 catctgtctg gcaacgctca ctctacaatg tgaatggact gaaagcacag ccttggtgga 1741 ccccaaaaga aacgggctac acagagttag taaagtcttt agaaagaaac tggaagttaa 1801 tccgagatga aggccttgca gtgatggata aagccaaagg tctcttcctg cctgaggatg 1861 aaaacctgag ggaaaaaggg gactggagcc agttcacgct gtggcagcaa ggaagaagaa 1921 atgaaaatgc ctgcaaagga gctcctaaaa cctgtacctt actagaaaag ttccccgaga 1981 caacaggatg cagaagagga cagatcaaat attccatcat gcaccccggg actcacgtgt 2041 ggccgcacac agggcccaca aactgcaggc tccgaatgca cctgggcttg gtgattccca 2101 aggaaggctg caagattcga tgtgccaacg agaccaggac ctgggaggaa ggcaaggtgc 2161 tcatctttga tgactccttt gagcacgagg tatggcagga tgcctcatct ttccggctga 2221 tattcatcgt ggatgtgtgg catccggaac tgacaccaca gcagagacgc agccttccag 2281 caatttagca tgaattcatg caagcttggg aaactctgga gaga
```

(SEQ ID NO: 2; GENBANK Accession No. S83325; codon encoding initiating methionine is underlined).

Clinical Use

Antigen-presenting cells (APCs) such as DCs are obtained from subjects, e.g., human patients suffering from or at risk of developing cancer, using the process of leuka-pheresis. Such as procedure is typically carried out at an apheresis center (Day 1). Dendritic cells are purified using known methods are contacted with antigen, such as AAH or AAH and AFP together. Following antigen contact, the cells are cultured with a mixture of cytokines (Day 2-3). The antigen-primed and activated DCs are then administered to the patient (Day 3-4). An exemplary course of therapy includes three administrations of DCs over a four week period.

The following materials and methods were used to generated the data described herein.

Animals 7-8-week-old female BALB/c (H-$2^d$) mice were purchased from Harlan Sprague Dawley, Inc., and kept under specific pathogen-free conditions.

Preparation of Magnetic Microbeads

Immunomagnetic beads (1.3 µm; Calbiochem) were washed three times with 50 mM borate buffer, pH 8.5, and resuspended in 50 mM borate buffer, pH 9.0, with 0.1 mg/ml AAH or GFP protein. Then the suspension was incubated overnight at room temperature under constant agitation. The beads were pelleted, washed with PBS, and resuspended in PBS at a concentration of 30 mg solid content/ml.

Isolation of DCs

DC isolation was performed using known methods (e.g., (Gehring et al., 2008, J. Immunol. Meth. 332:18-30)). Cells are optionally obtained by leukapheresis. 10 µg pUMVC3-hFLex, an expression plasmid encoding Fms-like tyrosine kinase receptor-3 ligand (FLT3L), was injected into the mouse tail vein on day 0 and 6. Splenocytes were prepared from the FLT3L-injected mice, using NH$_4$Cl red blood cell-lysis buffer, and 5×10$^7$ cells were incubated in serum-free DMEM with 10 µl magnetic microbeads for 4-6 hours. The cells were collected, passed through a magnetic field using MACS MS column (Miltenyi) to enrich the cells ingesting magnetic beads. Then the cells were subjected to density-gradient centrifugation using Lympholyte M (Cedarlane) to eliminate free beads and dead cells. The viable cells were collected, washed twice with Hanks' buffered salt solution (HBSS), and used for subsequent experiments. The viability of the isolated cells was >90%, and the percentage of the CD11c-positive population in the isolated cells were 70-80%.

Cell Culture

DCs were cultured in HEPES-buffered RPMI1640 supplemented with 10% mouse serum (Equitech Bio), 2 mM L-glutamine, 50 µM 2-mercaptoethanol, 100 U/ml penicillin, 100 µg/ml streptomycin, 20 ng/ml GMCSF, 100 ng/ml IL-4, 20 ng/ml IFN-γ, and 1 µg/ml CD40L (all cytokines were purchased from Peprotech) on a 6-well ultra-low attachment plate (Corning) for 40 h. For cytokine release, splenocytes were grown in serum-free X-VIVO 15 (Lonza) supplemented with 2 mM L-glutamine, 50 nM 2-mercaptoethanol, 100 U/ml penicillin, and 100 µg/ml streptomycin. For the cytotoxicity assay, splenocytes were grown in the complete medium consisting of HEPES-buffered RPMI1640 supplemented with 10% fetal bovine serum (Atlantic Bio), 2 mM L-glutamine, 50 µM 2-mercaptoethanol, 100 U/ml penicillin, 100 µg/ml streptomycin, 1× non-essential amino acids (Lonza), 0.5× amino acid solution (Invitrogen), and 1 mM sodium pyruvate. SP2/0 cells were cultured in Dulbecco's minimum essential medium supplemented with 20% fetal bovine serum, 2 mM L-glutamine, 100 U/ml penicillin, and 100 µg/ml streptomycin.

Enzyme-Linked Immunosorbent Assay (ELISA)

DCs or splenocytes were grown in the serum-free medium with or without AAH protein for 48 h. Then the culture supernatants were collected, centrifuged, and subjected to ELISA assays. ELISA for IL-12, p70, IFN-γ, and IL-4 was performed using ELISA Ready-SET-Go! kit (eBioscience) according to the manufacturer's instructions.

Flow Cytometry

The expression of cell surface markers was analyzed by flow cytometry as described previously (Gehring, et al., 2008). 3-6×10$^5$ cells were used for staining. The cells were washed with staining buffer (HBSS containing 5% FBS), incubated with 2.5 µg/ml Mouse BD Fc Block (BD Biosciences) for 5 min at 4° C., and further incubated with staining antibodies for 30 min at 4° C. The antibodies used were anti-CD11c (HL3; BD Biosciences), anti-CD40 (3/23; BD Biosciences), anti-CD54 (3E2; BD Biosciences), anti-CD80 (16-10A1; BD Biosciences), anti-CD 86 (GLI; BD Biosciences), anti-I-A$^d$ (AMS-32.1; BD Biosciences), and anti-CD8a (53-6.7; eBioscience), all of which were conjugated with fluorochrome. Hamster, rat, and mouse immunoglobulin G isotype-matched controls were also used for staining controls. After washing twice, the cells were resuspended in staining buffer, and were subjected to flow cytometry using FACSCalibur (BD Biosciences). Dead cells were eliminated from analysis by staining the cells with 7-amino-actinomycin D (eBioscience). Data were processed with CellQuest software (BD Biosciences) followed by FlowJo software (Tree Star).

Vaccination

After the culture with cytokines for 40 h, 2.5×10$^5$ cells were injected subcutaneously into the right and left flanks (5×10$^5$ cells per mouse) on day 0 and 14. On day 28, the immunized mice were used for further experiments including cytokine release and cytotoxicity assay.

Cytotoxicity Assay

Splenocytes were prepared from immunized mice, and 5×10$^7$ splenocytes were grown in complete medium with 0.5 µg/ml AAH protein for 2 days and further grown for 2 days after addition of 10 ng/ml IL-2. Two×10$^4$ target SP2/0 cells were mixed with 6-60×10$^4$ effector splenocytes in the serum-free medium, centrifuged at 200×g for 5 min, and incubated in CO$_2$ incubator for 4 h. Culture supernatants were collected, and released lactate dehydrogenase activity in the supernatants were measured by using LDH Cytotoxicity Detection Kit (Roche) in accordance with manufacturer's instruction. % target cell lysis was calculated using the following formula:

$$((A_{effector+target} - A_{effector} - A_{target}) \text{ divided by} (A_{target+TritonX} - A_{target})) \times 100,$$

where A indicates absorbance at 490 nm.

IL-12 Secretion by the Isolated DCs Stimulated by Various Cytokines In Vitro

The protocol previously used includes in vivo expansion of DCs, ingestion of magnetic microbeads on which an antigen and stimulants of DCs including LPS and anti-CD40 antibody are coated, and isolation of DCs by passing through a magnetic column. Instead of stimulating DCs with the stimulants coated on the beads, the improved method involved stimulating isolated DCs by growing for two days in the presence of various cytokines, because stimulants should interact with the corresponding receptors on the cell surface, but the stimulants on the beads that were ingested by DCs cannot. There exist some cytokines that stimulate and promote maturation of DCs including IL-4, IFN-γ, and CD40L. Therefore, the combinatorial effect of these cytokines on the maturation of DCs was examined. Expansion, ingestion, and isolation of DCs were performed. Isolated cells were cultured for 40 hours in the presence of GM-CSF and/or IL-4, and/or IFN-γ, and/or CD40L. GM-CSF was always added because it was necessary for survival of DCs. Mature, but not immature, DCs vigorously produce IL-12, which is essential for polarizing helper and cytotoxic T cells.

Therefore, IL-12 levels were used as an indicator of DC stimulation. Supernatants of the culture was collected, the concentration of IL-12 p70 was measured by ELISA. The results indicated that IL-12 p70 was the highest when all cytokines were present in the DC culture (FIG. 1). Each of the cytokines are used for stimulation alone or in combination. Preferably, all the cytokines are used to stimulate DCs. However, CD40L is optional.

Expression of Mature DC Markers on the Surface of Stimulated DCs

Figure 3:
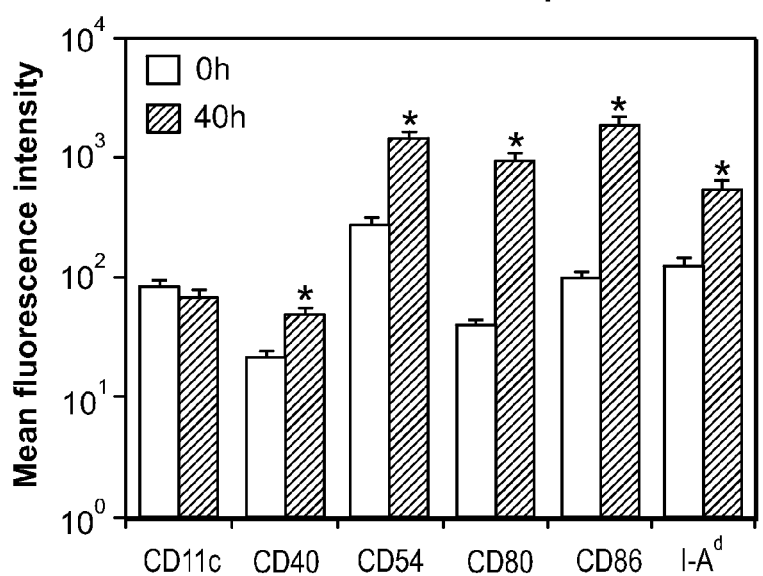
FIG. 3 is a bar graph showing mean fluorescence on surface DC markers.
Figure 2:
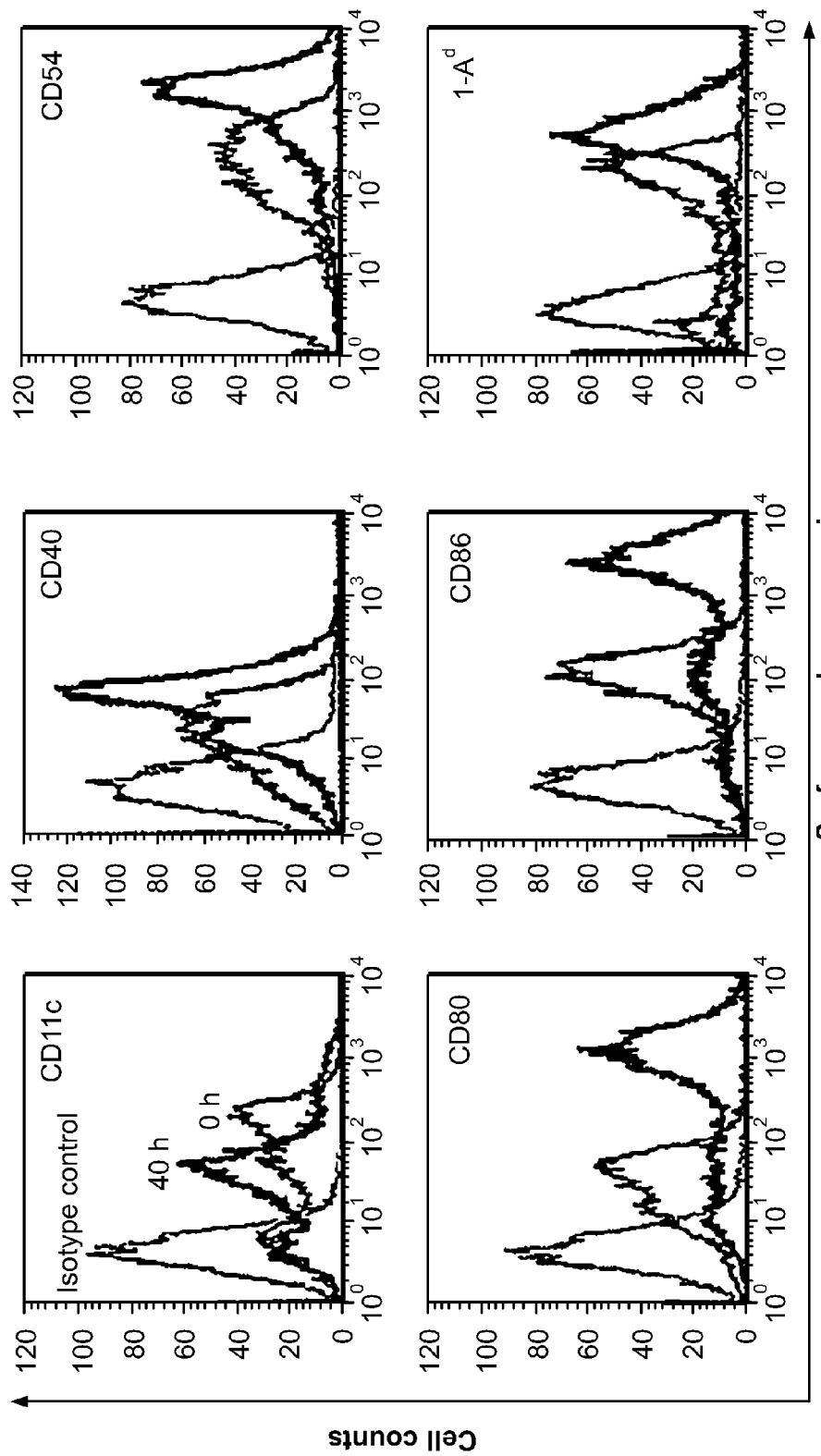
FIG. 2 is a series of line graphs showing expression of various surface DC markers on isolated DCs.
Figure 4:
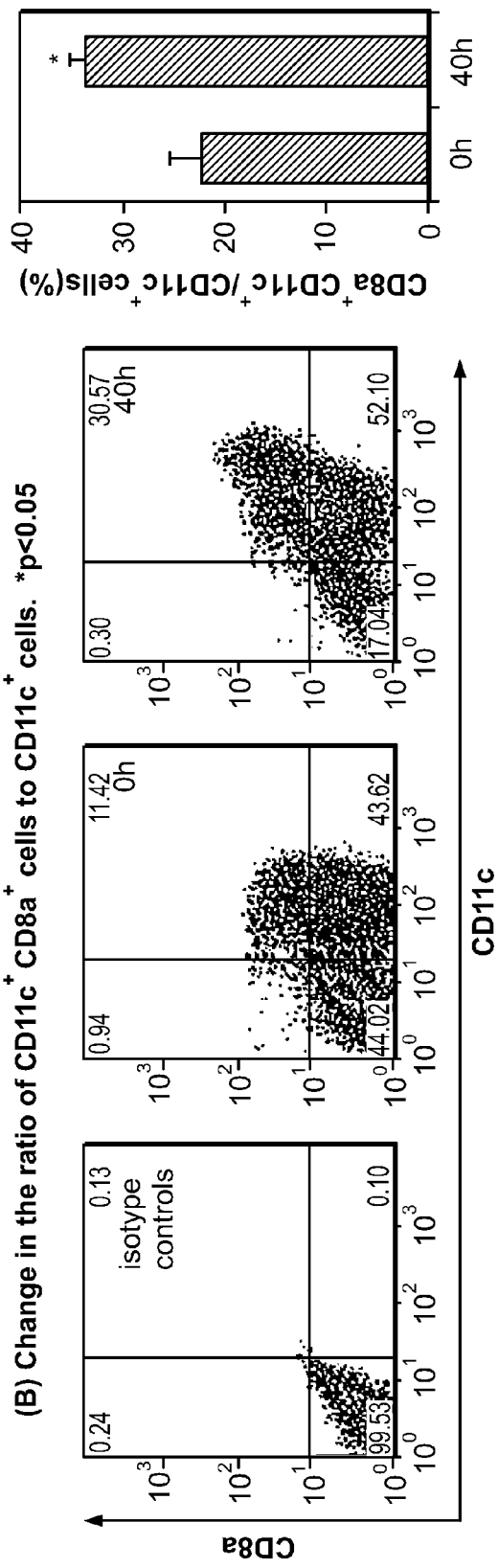
FIG. 4 is a series of flow cytometric graphs and a bar graph showing an increased population of CD8+ DCs grown in the presence of cytokines.

To investigate the effect of the cytokine stimulation on the expression of mature DC markers, the marker expression of DCs grown for 40 h in the presence of the cytokines to that of DCs without culture was measured. The expression of CD11c, a marker for pan-DCs, was not changed after the culture (FIGS. 2,3). However, all the mature DC markers including CD40, CD54, CD80, CD86, and MHC class II (I-A$^d$), were significantly up-regulated in the DCs grown for 40 h (FIGS. 2,3). CD8a$^+$ DCs are the subset of DCs that can efficiently stimulate CTLs. The effect of the cytokine stimulation on CD8a$^+$ DC population was evaluated. As shown in FIG. 4, the percentage of CD8a$^+$ population in DCs was significantly increased during the stimulation. These results indicate that the generated cells by this method without using LPS had sufficient quality for DC-based immunization.

Figure 5:
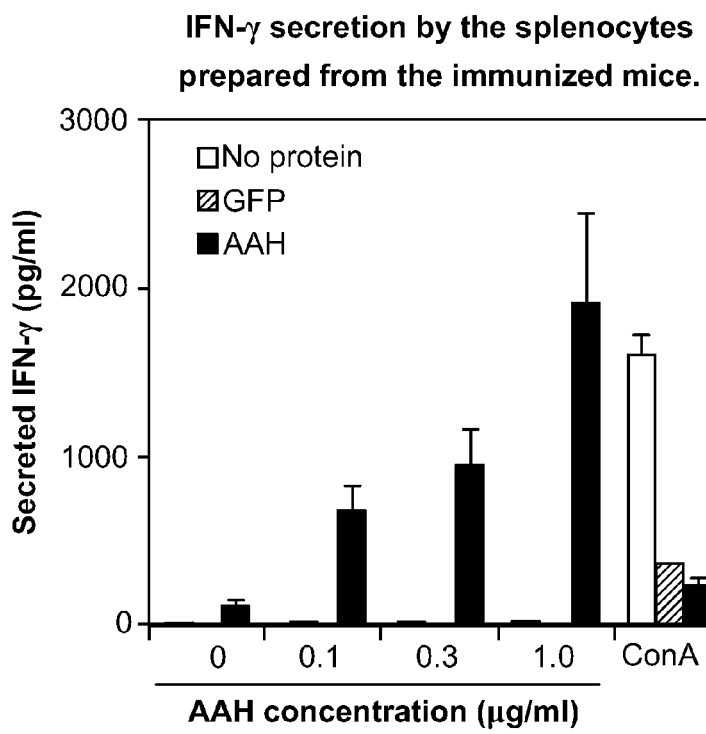
FIG. 5 is a bar graph showing IFN-γ secretion.

Secretion of IFN-γ in Response to AAH by the Splenocytes from AAH-Immunized Mice To examine whether $T_H1$ response was induced by the AAH immunization, the production of IFN-γ, a $T_H1$ cytokine, in response to AAH protein was measured. Mice were immunized twice with a 2-week interval with DCs ingesting AAH or GFP-coated beads, or beads without any antigens. Two weeks after the last immunization, splenocytes were prepared from the immunized mice, cultured for 48 h in the presence of AAH, and the concentration of IFN-γ was measured in culture supernatants to examine whether splenocytes from AAH-immunized mice produce IFN-γ in response to AAH stimulation. The splenocytes from AAHimmunized mice vigorously produced IFN-γ in a dose-dependent manner (FIG. 5). Although splenocytes from three groups produced considerable amount of IFN-γ in the presence of concanavalin A (Con A), the control splenocytes produced only subtle IFN-γ when stimulated with AAH (FIG. 5). This result indicates that $T_H1$ cells responsive to AAH were generated in the immunized mice.

Secretion of IL-4 in Response to AAH by the Splenocytes from AAH-Immunized Mice

Figure 6:
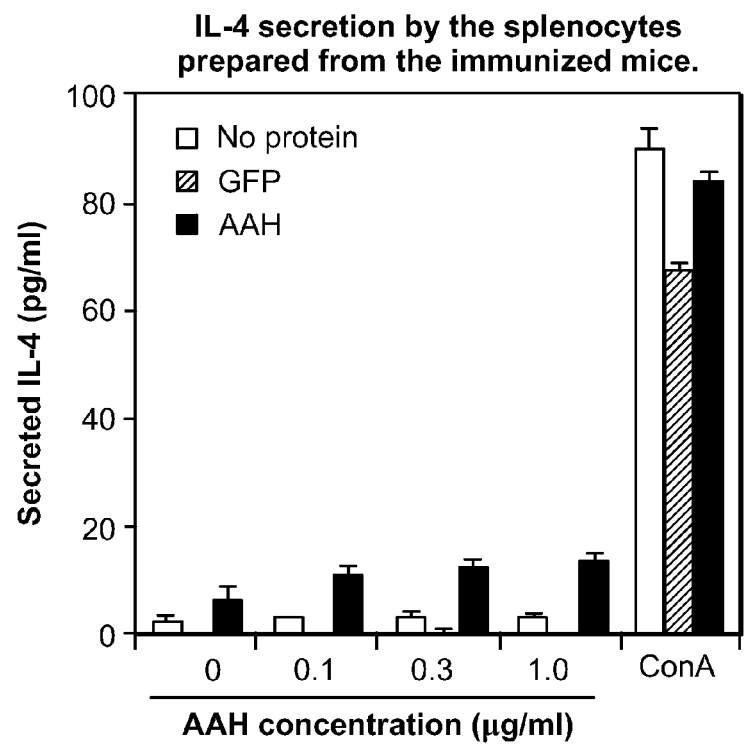
FIG. 6 is a bar graph showing IL-4 secretion.

To investigate whether humoral immunity against AAH was induced by the DCs loaded with AAH, the concentration of IL-4, a $T_H2$ cytokine, was measured in the same samples as IFN-γ. Con A-stimulated splenocytes produced large amount of IL-4 independent of the immunization (FIG. 6). By contrast, the splenocytes prepared from the mice immunized with three types of DCs produced only trace amounts of IL-4 (FIG. 6), indicating that $T_H2$ cells responsive to AAH were not efficiently induced by AAH immunization.

CTL Activity Against AAH-Expressing Cells in AAH-Immunized Mice

Figure 7:
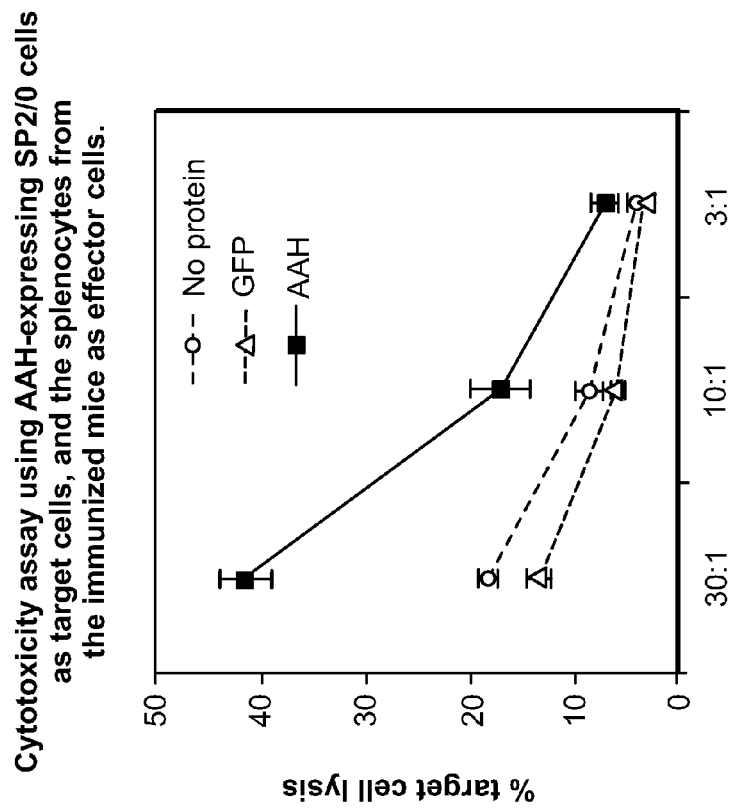
FIG. 7 is a line graph showing the results of a cytotoxicity assay.
Figure 8:
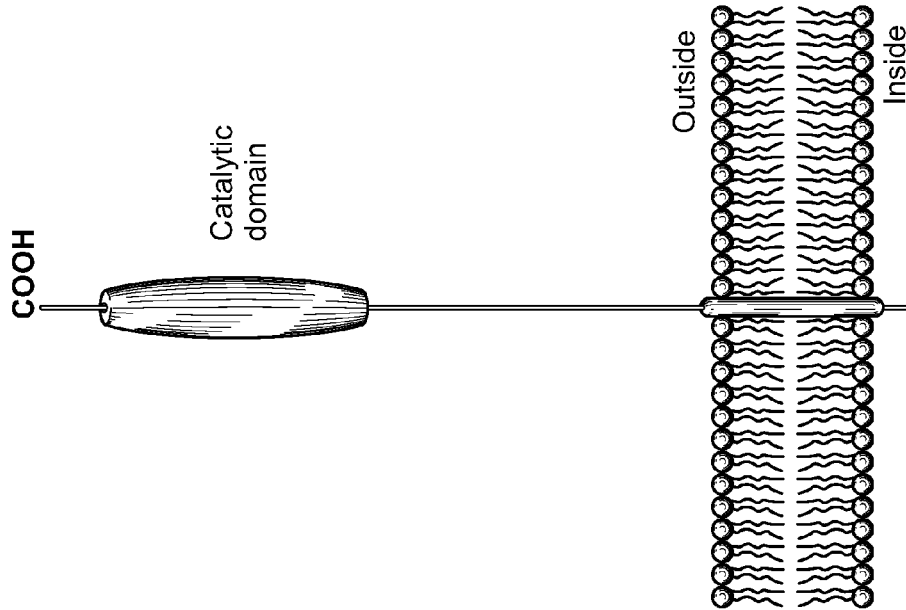
FIG. 8 is a diagram of AAH as expressed by a cell.
Figure 9:
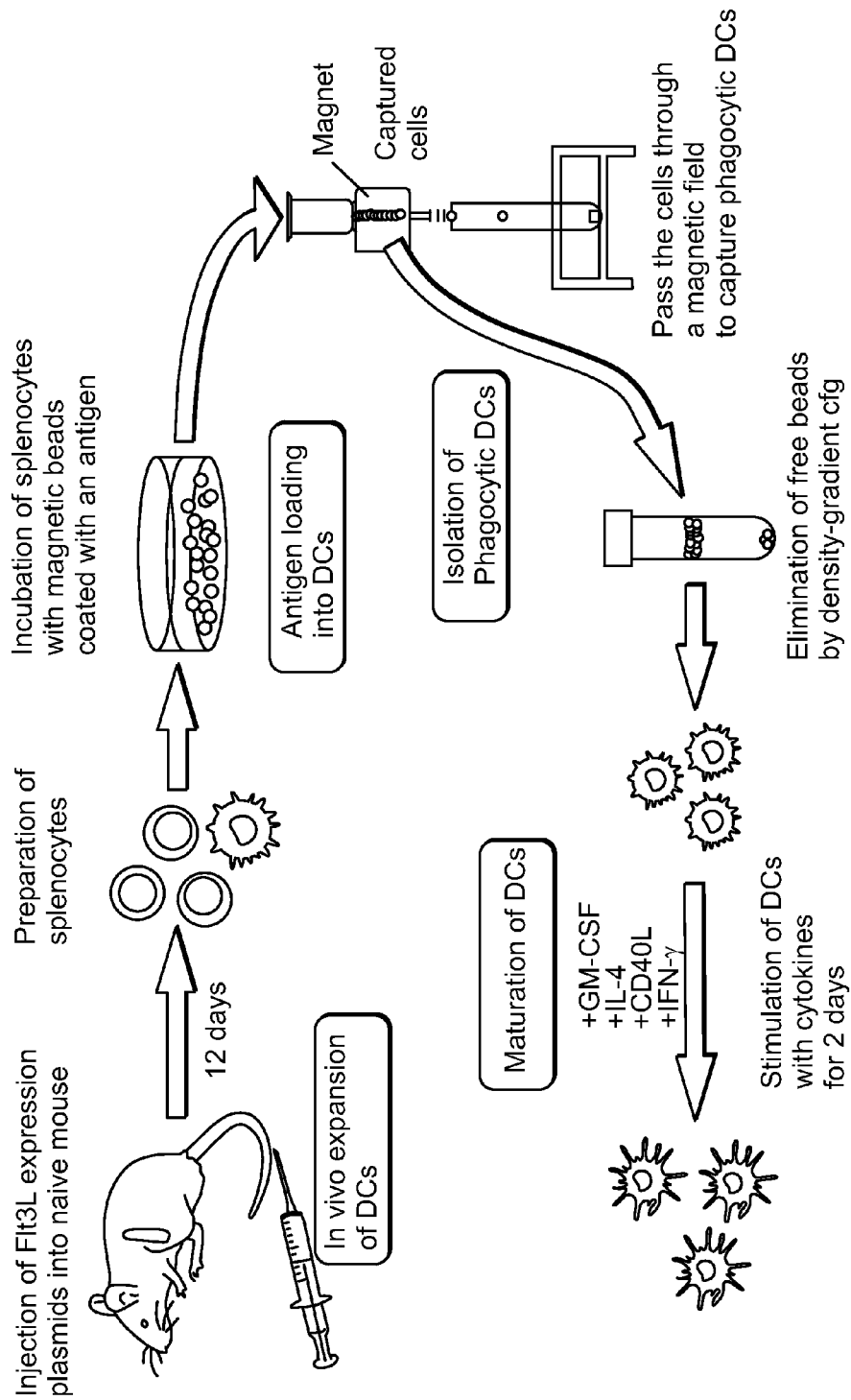
FIG. 9 is a diagram of a method of generating mature antigen-loaded DCs.
Figure 10:
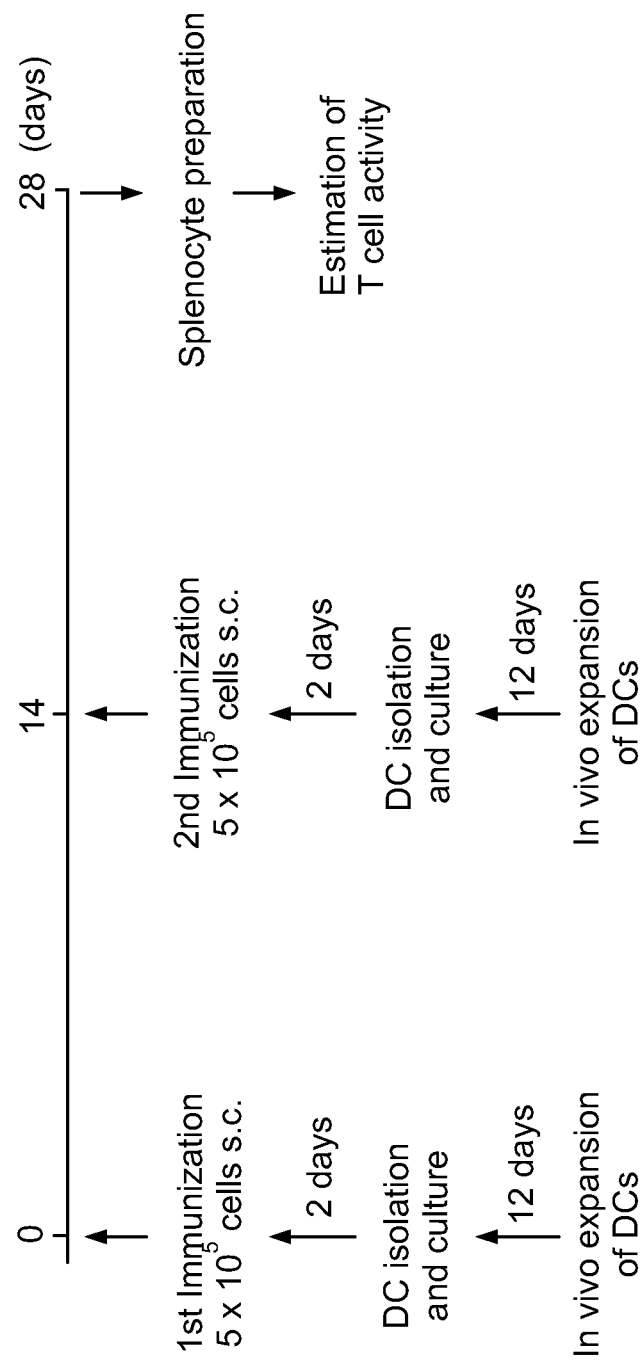
FIG. 10 is a flow chart of a schedule of immunization with AAH-loaded DCs.

To determine whether CTLs responsive to AAH were induced in AAH-immunized mice, cytotoxicity was evaluated by using AAH-expressing SP2/0 cells as target cells. SP2/0 cells were co-cultured for 4 h with the splenocytes from the immunized mice after activated with AAH protein and IL-2. The efficiencies of target cell lyses were estimated by measuring lactate dehydrogenase activities released from dying target cells. As shown in FIG. 7, the splenocytes from the AAH-immunized mice had more CTL activity than the other control splenocytes, suggesting that AAH immunization induced AAH-responsive CTLs.

AAH-Responsive T Cells in AAH-Immunized Mice

When mice were immunized with AAH-loaded DCs, AAH-responsive $T_H1$ cells and CTLs were induced. Antigen-specific T cell expansion is another important indicator that indicates that antigen-responsive T cells were produced.

Anti-Tumor Effect of AAH Immunization In Vivo

AAH immunization using AAH-primed DCs induces antitumor immunity. Mice are immunized with AAH-loaded DCs twice with a 2-week interval, and two weeks after the last immunization. SP2/0 cells are implanted under the skin, the growth of implanted tumor sizes is measured. Data obtained from this tumor burden model reflects the preventive effect of the immunization. To evaluate the curative effect of AAH immunization, SP2/0 cells are implanted first, then when tumors grow to 5 mm in diameter, the mice are immunized with AAH-loaded DCs, and the effect on tumor growth measured.

AAH-targeted immunotherapy also suppresses metastasis. Mice are immunized with AAH-loaded DCs followed by injection of SP2/0 cells into the tail vein. Two weeks later, the lungs are excised to count the number of nodules formed. A reduction in the amount of nodules in immunized mice compared to the amount in unimmunized mice indicates that the AAH-loaded DC immunization regimen suppresses metastasis of AAH-bearing tumors.

Figure 11:
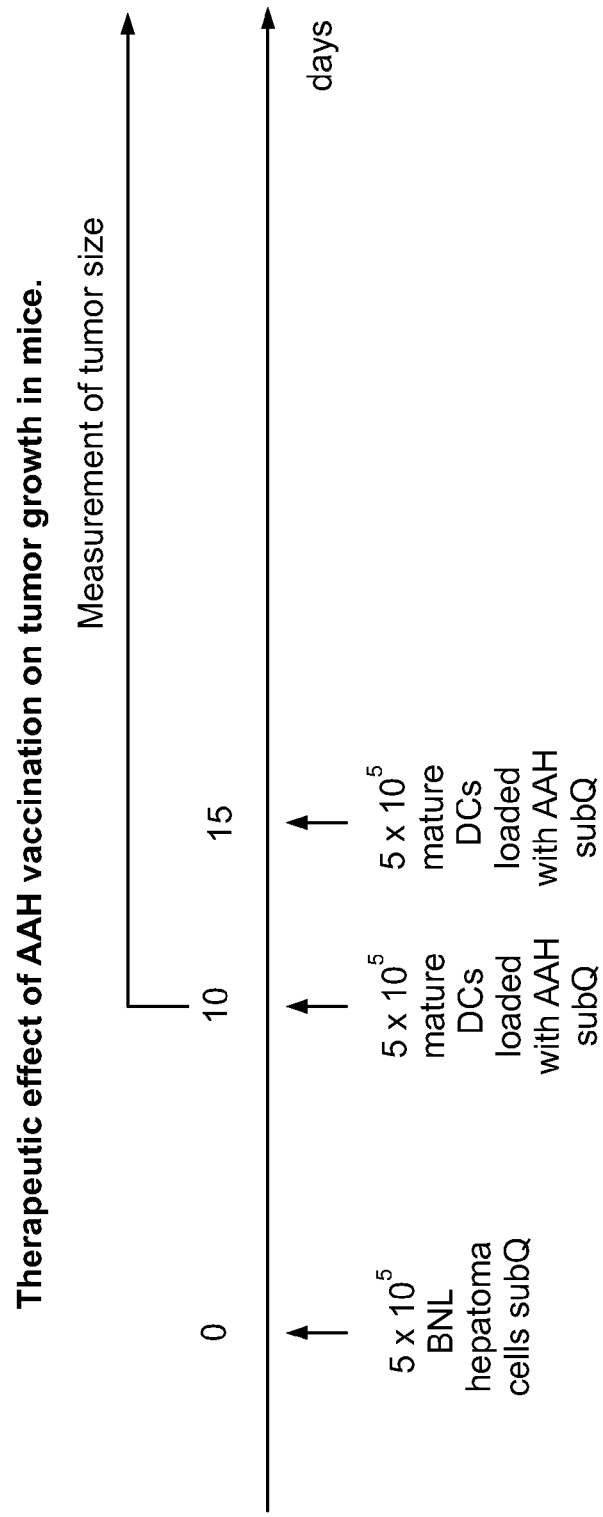
FIG. 11 is a diagram showing a protocol for determining the therapeutic effect of AAH vaccination on tumor growth in mice.
Figure 12:
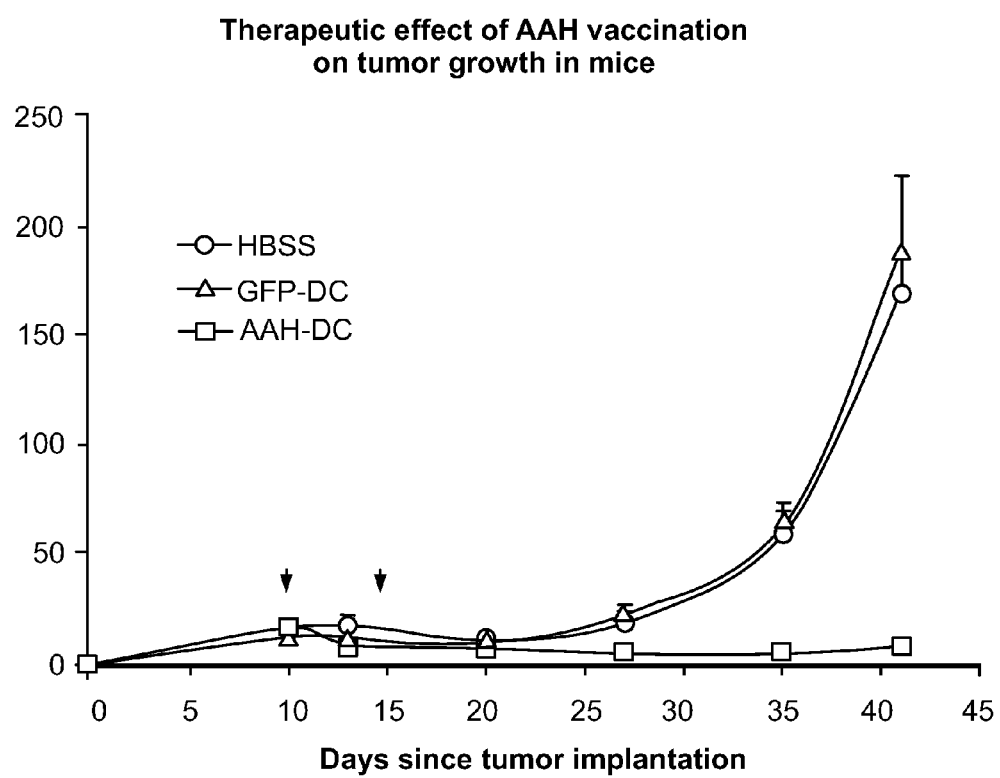
FIG. 12 is a line graph showing therapeutic effect of AAH vaccination on tumor growth in mice.

Vaccination with AAH-loaded mature dendritic cells dramatically reduced tumor burden (tumor volume) of an AAH-expressing tumor. The therapeutic effect of AAH vaccination on the growth of tumor in mice is shown in FIGS. 11 and 12. 5×10$^5$ BNL 1ME A.7R.1 mouse hepatoma cells were subcutaneously implanted into the flanks of 6-week-old BALB/c mice. At day 10 and 15, 5×10$^5$ mature DCs loaded with AAH or GFP, or HBSS were subcutaneously injected into the tumor-bearing mice. Tumor size was measure weekly. Tumor volumes were determined by the following formula: 0.52×(length)×(width)$^2$. Each data point represents the mean tumor volume±standard error (n=6). Tumor volumes were found to be significantly reduced following immunization with AAH-loaded DCs. These data using an art-recognized tumor model indicate that a therapeutic method using AAH-loaded mature DCs is effective to reduce and eliminate AAH-bearing tumors in vivo. Such dendritic cell vaccines demonstrate potent anti-tumor effects against any AAH-expressing tumors.

Augmentation of Anti-Tumor Effect by Simultaneously Immunizing AAH and AFP

AFP is the only HCC-associated protein that can be antigenic to mice and humans. However, it has been shown as well that the anti-tumor effect is not sufficient for human HCC patients. However, simultaneous immunization with AAH and AFP augments the immune response to tumors expressing both AAH and AFP, like HCC.

Stable lines of AFP-expressing SP2/0 cells are made by introducing an AFP expression plasmid DNA. By using the cells, CTL activity in vitro in the mice immunized with AFP-loaded and AAH-loaded DCs is measured. Increased cytotoxicity following immunization indicates that immunization lead to an anti-tumor effect of combination AAH and AFP immunization on the growth AAH and/or AFP-bearing tumors.

The invention claimed is:

1. A method of reducing growth of an aspartyl (asparaginyl)-β-hydroxylase (AAH)-expressing tumor in a subject, comprising providing an isolated mature AAH-loaded dendritic cell and administering to said subject said isolated mature AAH-loaded dendritic cell, wherein growth of said AAH-expressing tumor is reduced after administration of said dendritic cell, and wherein said dendritic cell is primed by contact with an AAH followed by contact with a combination of cytokines comprising GM-CSF (Granulocyte-macrophage colony stimulating factor), CD40L (Cluster of Differentiation 40 ligand), and IFN-γ (interferon gamma) ex vivo, prior to said administering to said subject.

2. The method of claim 1, wherein said tumor is selected from the group consisting of liver, gastrointestinal, pancreas, breast, prostate, cervix, ovary, fallopian tube, larynx, lung, thyroid, gall bladder, kidney, bladder, and brain cancers.

3. The method of claim 1, wherein said dendritic cells are contacted with said combination of cytokines for at least 10 hours.

4. The method of claim 1, wherein said dendritic cells are contacted with said combination of cytokines for at least 40 hours.

5. The method of claim 1, wherein said subject is a human, canine, feline, equine, bovine, or porcine subject.

6. The method of claim 1, wherein said AAH-expressing tumor is a liver cancer.

7. The method of claim 6, wherein said liver cancer comprises hepatocellular carcinoma or cholangiocarcinoma.

8. A method of producing primed dendritic cells, comprising contacting isolated dendritic cells with an antigen comprising AAH (aspartyl (asparaginyl)-β-hydroxylase), and following said antigen-contacting step, contacting said dendritic cells with a combination of cytokines, said combination comprising GM-CSF (Granulocyte-macrophage colony stimulating factor), CD40L (Cluster of Differentiation 40 ligand), and IFN-γ (interferon gamma).

9. The method of claim 8, wherein said combination further comprises IL-4 (Interleukin-4).

10. The method of claim 8, wherein said antigen is in a soluble form.

11. The method of claim 8, wherein said dendritic cells are obtained from a subject by leukapheresis.

12. The method of claim 11, wherein said subject is suffering from an AAH-bearing tumor.

13. A vaccine composition comprising primed dendritic cells produced by the method of claim 8.

14. A method of inhibiting tumor growth in a mammal, comprising identifying a subject suffering from an AAH (aspartyl (asparaginyl)-β-hydroxylase)-bearing tumor, and administering to said subject autologous dendritic cells, wherein said autologous dendritic cells are primed according to the method of claim 8.

15. A method of preventing metastasis of an AAH (aspartyl (asparaginyl)-β-hydroxylase)-bearing tumor, comprising identifying a subject suffering from an AAH-bearing tumor, and administering to said subject autologous dendritic cells, wherein said autologous dendritic cells are primed according to the method of claim 8.

16. A method of producing primed dendritic cells, comprising contacting isolated dendritic cells with an antigen comprising AAH (aspartyl (asparaginyl)-β-hydroxylase) and AFP (α-fetoprotein), and following said antigen-contacting step, contacting said dendritic cells with a combination of cytokines, said combination comprising GM-CSF (Granulocyte-macrophage colony stimulating factor) and IFN-γ (interferon gamma).

17. A method of producing primed dendritic cells, comprising contacting isolated dendritic cells with an antigen comprising AAH (aspartyl (asparaginyl)-β-hydroxylase), and following said antigen-contacting step, contacting said dendritic cells with a combination of cytokines, said combination comprising GM-CSF (Granulocyte-macrophage colony stimulating factor), CD40L (Cluster of Differentiation 40 ligand) and IFN-γ (interferon gamma), and wherein said antigen is bound to a biodegradable solid support.

18. A method of producing primed dendritic cells, comprising contacting isolated dendritic cells with an antigen comprising AAH (aspartyl (asparaginyl)-β-hydroxylase), and following said antigen-contacting step, contacting said dendritic cells with a combination of cytokines, said combination comprising GM-CSF (Granulocyte-macrophage colony stimulating factor), CD40L (Cluster of Differentiation 40 ligand) and IFN-γ (interferon gamma), and wherein said antigen is bound to a solid support, wherein said solid support comprises a polystyrene bead.

19. A vaccine containing AAH-loaded mature dendritic cells for treatment of AAH-expressing tumors in a mammalian subject, wherein said dendritic cells are primed by contact with an AAH followed by contact with a combination of cytokines comprising GM-CSF (Granulocyte-macrophage colony stimulating factor), CD40L (Cluster of Differentiation 40 ligand) and IFN-γ (interferon gamma).

20. A method of reducing growth of an aspartyl (asparaginyl)-β-hydroxylase (AAH)-expressing tumor in a subject, comprising administering to said subject an isolated mature AAH-loaded dendritic cell, wherein growth of said AAH-expressing tumor is reduced after administration of said dendritic cell, and wherein said dendritic cell is activated with a combination of cytokines comprising GM-CSF and IFN-γ ex viva, prior to said administering to said subject, wherein said dendritic cell is further loaded with AFP.

21. A method of reducing growth of an aspartyl (asparaginyl)-β-hydroxylase (AAH)-expressing AAH-expressing liver tumor in a subject, comprising providing an isolated mature AAH-loaded dendritic cell and administering to said subject said isolated mature AAH-loaded dendritic cell, wherein growth of said AAH-expressing tumor is reduced after administration of said dendritic cell, and wherein said dendritic cell is primed by contact with an AAH and a combination of cytokines comprising GM-CSF (Granulocyte-macrophage colony stimulating factor), CD40L (Cluster of Differentiation 40 ligand), interleukin-4 (IL-4) and IFN-γ (interferon gamma) ex viva, prior to said administering to said subject.

22. The method of claim 21, wherein said AAH-expressing liver tumor comprises hepatocellular carcinoma or cholangiocarcinoma.

* * * * *

SEQUENCE LISTING

<160> NUMBER OF SEQ ID NOS: 2

<210> SEQ ID NO 1
<211> LENGTH: 758
<212> TYPE: PRT
<213> ORGANISM: Homo sapiens

<400> SEQUENCE: 1

```
Met Ala Gln Arg Lys Asn Ala Lys Ser Ser Gly Asn Ser Ser Ser Ser
1               5                   10                  15

Gly Ser Gly Ser Gly Ser Thr Ser Ala Gly Ser Ser Pro Gly Ala
            20                  25                  30

Arg Arg Glu Thr Lys His Gly Gly His Lys Asn Gly Arg Lys Gly Gly
        35                  40                  45

Leu Ser Gly Thr Ser Phe Phe Thr Trp Phe Met Val Ile Ala Leu Leu
    50                  55                  60

Gly Val Trp Thr Ser Val Ala Val Val Trp Phe Asp Leu Val Asp Tyr
65                  70                  75                  80

Glu Glu Val Leu Gly Lys Leu Gly Ile Tyr Asp Ala Asp Gly Asp Gly
                85                  90                  95

Asp Phe Asp Val Asp Asp Ala Lys Val Leu Leu Gly Leu Lys Glu Arg
            100                 105                 110

Ser Thr Ser Glu Pro Ala Val Pro Pro Glu Glu Ala Glu Pro His Thr
        115                 120                 125

Glu Pro Glu Glu Gln Val Pro Val Glu Ala Glu Pro Gln Asn Ile Glu
    130                 135                 140

Asp Glu Ala Lys Glu Gln Ile Gln Ser Leu Leu His Glu Met Val His
145                 150                 155                 160

Ala Glu His Val Glu Gly Glu Asp Leu Gln Gln Glu Asp Gly Pro Thr
                165                 170                 175

Gly Glu Pro Gln Gln Glu Asp Asp Glu Phe Leu Met Ala Thr Asp Val
            180                 185                 190

Asp Asp Arg Phe Glu Thr Leu Glu Pro Glu Val Ser His Glu Glu Thr
        195                 200                 205

Glu His Ser Tyr His Val Glu Glu Thr Val Ser Gln Asp Cys Asn Gln
    210                 215                 220

Asp Met Glu Glu Met Met Ser Glu Gln Glu Asn Pro Asp Ser Ser Glu
225                 230                 235                 240

Pro Val Val Glu Asp Glu Arg Leu His His Asp Thr Asp Asp Val Thr
                245                 250                 255

Tyr Gln Val Tyr Glu Glu Gln Ala Val Tyr Glu Pro Leu Glu Asn Glu
            260                 265                 270

Gly Ile Glu Ile Thr Glu Val Thr Ala Pro Pro Glu Asp Asn Pro Val
        275                 280                 285

Glu Asp Ser Gln Val Ile Val Glu Glu Val Ser Ile Phe Pro Val Glu
    290                 295                 300

Glu Gln Gln Glu Val Pro Pro Glu Thr Asn Arg Lys Thr Asp Asp Pro
305                 310                 315                 320

Glu Gln Lys Ala Lys Val Lys Lys Lys Pro Lys Leu Leu Asn Lys
                325                 330                 335

Phe Asp Lys Thr Ile Lys Ala Glu Leu Asp Ala Ala Glu Lys Leu Arg
            340                 345                 350

Lys Arg Gly Lys Ile Glu Glu Ala Val Asn Ala Phe Lys Glu Leu Val
        355                 360                 365

Arg Lys Tyr Pro Gln Ser Pro Arg Ala Arg Tyr Gly Lys Ala Gln Cys
```

```
                370                 375                 380
Glu Asp Asp Leu Ala Glu Lys Arg Arg Ser Asn Glu Val Leu Arg Gly
385                 390                 395                 400

Ala Ile Glu Thr Tyr Gln Glu Val Ala Ser Leu Pro Asp Val Pro Ala
                405                 410                 415

Asp Leu Leu Lys Leu Ser Leu Lys Arg Ser Asp Arg Gln Gln Phe
                420                 425                 430

Leu Gly His Met Arg Gly Ser Leu Leu Thr Leu Gln Arg Leu Val Gln
                435                 440                 445

Leu Phe Pro Asn Asp Thr Ser Leu Lys Asn Asp Leu Gly Val Gly Tyr
450                 455                 460

Leu Leu Ile Gly Asp Asn Asp Asn Ala Lys Lys Val Tyr Glu Glu Val
465                 470                 475                 480

Leu Ser Val Thr Pro Asn Asp Gly Phe Ala Lys Val His Tyr Gly Phe
                485                 490                 495

Ile Leu Lys Ala Gln Asn Lys Ile Ala Glu Ser Ile Pro Tyr Leu Lys
                500                 505                 510

Glu Gly Ile Glu Ser Gly Asp Pro Gly Thr Asp Asp Gly Arg Phe Tyr
                515                 520                 525

Phe His Leu Gly Asp Ala Met Gln Arg Val Gly Asn Lys Glu Ala Tyr
                530                 535                 540

Lys Trp Tyr Glu Leu Gly His Lys Arg Gly His Phe Ala Ser Val Trp
545                 550                 555                 560

Gln Arg Ser Leu Tyr Asn Val Asn Gly Leu Lys Ala Gln Pro Trp Trp
                565                 570                 575

Thr Pro Lys Glu Thr Gly Tyr Thr Glu Leu Val Lys Ser Leu Glu Arg
                580                 585                 590

Asn Trp Lys Leu Ile Arg Asp Glu Gly Leu Ala Val Met Asp Lys Ala
                595                 600                 605

Lys Gly Leu Phe Leu Pro Glu Asp Glu Asn Leu Arg Glu Lys Gly Asp
                610                 615                 620

Trp Ser Gln Phe Thr Leu Trp Gln Gln Gly Arg Arg Asn Glu Asn Ala
625                 630                 635                 640

Cys Lys Gly Ala Pro Lys Thr Cys Thr Leu Leu Glu Lys Phe Pro Glu
                645                 650                 655

Thr Thr Gly Cys Arg Arg Gly Gln Ile Lys Tyr Ser Ile Met His Pro
                660                 665                 670

Gly Thr His Val Trp Pro His Thr Gly Pro Thr Asn Cys Arg Leu Arg
                675                 680                 685

Met His Leu Gly Leu Val Ile Pro Lys Glu Gly Cys Lys Ile Arg Cys
690                 695                 700

Ala Asn Glu Thr Arg Thr Trp Glu Glu Gly Lys Val Leu Ile Phe Asp
705                 710                 715                 720

Asp Ser Phe Glu His Glu Val Trp Gln Asp Ala Ser Ser Phe Arg Leu
                725                 730                 735

Ile Phe Ile Val Asp Val Trp His Pro Glu Leu Thr Pro Gln Gln Arg
                740                 745                 750

Arg Ser Leu Pro Ala Ile
                755
<210> SEQ ID NO 2
<211> LENGTH: 2324
<212> TYPE: DNA
<213> ORGANISM: Homo sapiens

<400> SEQUENCE: 2
```

```
cggaccgtgc aatggcccag cgtaagaatg ccaagagcag cggcaacagc agcagcagcg        60
gctccggcag cggtagcacg agtgcgggca gcagcagccc cggggcccgg agagagacaa       120
agcatggagg acacaagaat gggaggaaag gcggactctc gggaacttca ttcttcacgt       180
ggtttatggt gattgcattg ctgggcgtct ggacatctgt agctgtcgtt tggtttgatc       240
ttgttgacta tgaggaagtt ctaggaaaac taggaatcta tgatgctgat ggtgatggag       300
attttgatgt ggatgatgcc aaagttttat taggacttaa agagagatct acttcagagc       360
cagcagtccc gccagaagag gctgagccac acactgagcc cgaggagcag gttcctgtgg       420
aggcagaacc ccagaatatc gaagatgaag caaaagaaca aattcagtcc cttctccatg       480
aaatggtaca cgcagaacat gttgagggag aagacttgca acaagaagat ggacccacag       540
gagaaccaca acaagaggat gatgagtttc ttatggcgac tgatgtagat gatagatttg       600
agaccctgga acctgaagta tctcatgaag aaaccgagca tagttaccac gtggaagaga       660
cagtttcaca agactgtaat caggatatgg aagagatgat gtctgagcag gaaaatccag       720
attccagtga accagtagta gaagatgaaa gattgcacca tgatacagat gatgtaacat       780
accaagtcta tgaggaacaa gcagtatatg aacctctaga aaatgaaggg atagaaatca       840
cagaagtaac tgctccccct gaggataatc ctgtagaaga ttcacaggta attgtagaag       900
aagtaagcat ttttcctgtg gaagaacagc aggaagtacc accagaaaca aatagaaaaa       960
cagatgatcc agaacaaaaa gcaaaagtta agaaaagaa gcctaaactt ttaaataaat      1020
ttgataagac tattaaagct gaacttgatg ctgcagaaaa actccgtaaa aggggaaaaa      1080
ttgaggaagc agtgaatgca tttaaagaac tagtacgcaa ataccctcag agtccacgag      1140
caagatatgg gaaggcgcag tgtgaggatg atttggctga aagaggaga agtaatgagg      1200
tgctacgtgg agccatcgag acctaccaag aggtggccag cctacctgat gtccctgcag      1260
acctgctgaa gctgagtttg aagcgtcgct cagacaggca acaatttcta ggtcatatga      1320
gaggttccct gcttaccctg cagagattag ttcaactatt tcccaatgat acttccttaa      1380
aaaatgacct tggcgtggga tacctcttga taggagataa tgacaatgca aagaaagttt      1440
atgaagaggt gctgagtgtg acacctaatg atggctttgc taaagtccat tatggcttca      1500
tcctgaaggc acagaacaaa attgctgaga gcatcccata tttaaaggaa ggaatagaat      1560
ccggagatcc tggcactgat gatggagat tttatttcca cctgggggat gccatgcaga      1620
gggttgggaa caagaggca tataagtggt atgagcttgg gcacaagaga ggacactttg      1680
catctgtctg gcaacgctca ctctacaatg tgaatggact gaaagcacag ccttggtgga      1740
ccccaaaaga aacgggctac acagagttag taaagtcttt agaaagaaac tggaagttaa      1800
tccgagatga aggccttgca gtgatggata agccaaagg tctcttcctg cctgaggatg      1860
aaaacctgag ggaaaaggg gactggagcc agttcacgct gtggcagcaa ggaagaagaa      1920
atgaaaatgc ctgcaaagga gctcctaaaa cctgtacctt actagaaaag ttccccgaga      1980
caacaggatg cagaagagga cagatcaaat attccatcat gcaccccggg actcacgtgt      2040
ggccgcacac agggcccaca aactgcaggc tccgaatgca cctgggcttg gtgattccca      2100
aggaaggctg caagattcga tgtgccaacg agaccaggac ctgggaggaa ggcaaggtgc      2160
tcatctttga tgactccttt gagcacgagg tatggcagga tgcctcatct ttccggctga      2220
tattcatcgt ggatgtgtgg catccggaac tgacaccaca gcagagacgc agccttccag      2280
caatttagca tgaattcatg caagcttggg aaactctgga gaga                       2324
```